(12) United States Patent
Kozuka et al.

(10) Patent No.: US 10,379,076 B2
(45) Date of Patent: Aug. 13, 2019

(54) ELECTRICALLY CONDUCTIVE OXIDE SINTERED COMPACT, MEMBER FOR ELECTRICAL CONDUCTION, AND GAS SENSOR

(71) Applicant: NGK SPARK PLUG CO., LTD., Nagoya-shi, Aichi (JP)

(72) Inventors: Hisashi Kozuka, Ichinomiya (JP); Mina Sato, Komaki (JP); Yasuyuki Okimura, Inuyama (JP); Kazushige Ohbayashi, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 15 days.

(21) Appl. No.: 15/572,853

(22) PCT Filed: Mar. 28, 2016

(86) PCT No.: PCT/JP2016/001790
§ 371 (c)(1),
(2) Date: Nov. 9, 2017

(87) PCT Pub. No.: WO2016/181598
PCT Pub. Date: Nov. 17, 2016

(65) Prior Publication Data
US 2018/0106754 A1 Apr. 19, 2018

(30) Foreign Application Priority Data

May 13, 2015 (JP) ................................. 2015-097958

(51) Int. Cl.
| | | |
|---|---|---|
| *C01F 17/00* | (2006.01) | |
| *G01N 27/407* | (2006.01) | |
| *H01B 1/08* | (2006.01) | |
| *C04B 35/01* | (2006.01) | |
| *C04B 35/26* | (2006.01) | |
| *H01L 35/22* | (2006.01) | |

(52) U.S. Cl.
CPC ..... *G01N 27/4076* (2013.01); *C01F 17/0018* (2013.01); *C04B 35/01* (2013.01); *C04B 35/2608* (2013.01); *G01N 27/4075* (2013.01); *H01B 1/08* (2013.01); *C04B 2235/3227* (2013.01); *C04B 2235/3275* (2013.01); *C04B 2235/3279* (2013.01); *C04B 2235/72* (2013.01); *C04B 2235/725* (2013.01); *C04B 2235/768* (2013.01); *C04B 2235/80* (2013.01); *H01L 35/22* (2013.01)

(58) Field of Classification Search
None
See application file for complete search history.

(56) References Cited

U.S. PATENT DOCUMENTS

| | | |
|---|---|---|
| 6,054,403 A | 4/2000 | Kawase et al. |
| 2015/0099142 A1 | 4/2015 | Kozuka et al. |

FOREIGN PATENT DOCUMENTS

| | | |
|---|---|---|
| JP | 51-16089 A | 2/1976 |
| JP | 2-269949 A | 11/1990 |
| JP | 3-165253 A | 7/1991 |
| JP | 2002-84006 A | 3/2002 |
| JP | 2002-87882 A | 3/2002 |
| JP | 3286906 B2 | 5/2002 |
| WO | 2013/150779 A1 | 10/2013 |

OTHER PUBLICATIONS

Taguchi et al. Characterization of LaNixCoyFe1-x-yO3 as a cathode material for solid oxide fuel cells. Solid State Ionics 182 (2011) 127-132 (Year: 2011).*
Thuy et al. Structural, Electrical, and Ethanol-Sensing Properties of La1-xNdxFeO3 Nanoparticles, Advances in Materials Science and Engineering, vol. 2014, 5 pages (Year: 2014).*
Arakawa, T. Chapter 18: Perovskite Oxides as Solid State Chemical Sensors, Properties and Applications of Perovskite-Type Oxides, Tejuca & Fierro, CRC Press, Oct. 2000 (Year: 2000).*
Niwa, Eiki et al: "Conductivity and sintering property of $LaNi_{1-x}Fe_xO_3$ ceramics prepared by Pechini method", Solid State Ionics, 2011,vol. 201, Issue 1, p. 87-93, ISSN 0167-2738, (7 pages total).
Julphunthong, P. et al., "The Effects of Firing Temperatures and Dwell Time on Phase and Morphology Evolution of $LaNi_{0.6}Fe_{0.4}O_3$ Ceramics Prepared via the Combustion Technique", Ferroelectrics, 2013, vol. 454, Issue 1, 135-144, (10 pages total).
International Search Report dated May 10, 2016, issued by the International Searching Authority in counterpart International Application No. PCT/JP2016/001790 (PCT/ISA/210).
Written Opinion dated May 10, 2016, issued by the International Searching Authority in counterpart International Application No. PCT/JP2016/001790 (PCT/ISA/237).

\* cited by examiner

*Primary Examiner* — Tanisha Diggs
(74) *Attorney, Agent, or Firm* — Sughrue Mion, PLLC

(57) ABSTRACT

A gas sensor, characterized by having an electrode formed of a conductive oxide sintered body which contains a primary phase formed of a perovskite oxide containing at least La, Fe, and Ni; and a secondary phase formed of an $La_4M_3O_{10}$ phase or an $La_3M_2O_7$ phase (M=Co, Fe, Ni), wherein the conductive oxide sintered body has a conductivity of 300 S/cm or higher at room temperature.

2 Claims, 11 Drawing Sheets

| SAMPLE | $La_aCo_bFe_cNi_dO_x$ ELEMENTS (MOLE RATIO) | | | | CRYSTALLINE PHASE | | | | MAX. PEAK CRYSTALLINE PHASE | CONDUCTIVITY σ 25°C (S/cm) |
|---|---|---|---|---|---|---|---|---|---|---|
| | a | b | c | d | $LaMO_3$ | $La_4M_3O_{10}$ OR $La_3M_2O_7$ | $La_2MO_4$ | NiO | | |
| S1* | 0.500 | 0.000 | 0.400 | 0.100 | ○ | — | — | — | | 0.52 |
| S2* | 0.500 | 0.000 | 0.320 | 0.180 | ○ | — | — | — | PEROVSKITE | 56 |
| S3* | 0.500 | 0.000 | 0.250 | 0.250 | ○ | — | — | — | | 298 |
| S4 | 0.500 | 0.000 | 0.230 | 0.270 | ○ | ○ | — | — | | 540 |
| S5 | 0.500 | 0.000 | 0.225 | 0.275 | ○ | ○ | — | — | | 581 |
| S6 | 0.500 | 0.000 | 0.200 | 0.300 | ○ | ○ | — | — | | 821 |
| S7 | 0.500 | 0.000 | 0.150 | 0.350 | ○ | ○ | — | ○ | | 363 |
| S8* | 0.500 | 0.000 | 0.100 | 0.400 | ○ | ○ | — | ○ | $La_4M_3O_{10}$ OR $La_3M_2O_7$ | 175 |
| S9* | 0.500 | 0.000 | 0.050 | 0.450 | ○ | ○ | ○ | ○ | | 75 |
| S10* | 0.500 | 0.000 | 0.000 | 0.500 | — | — | ○ | ○ | $La_2NiO_4$ | 25 |
| S11* | 0.500 | 0.050 | 0.250 | 0.200 | ○ | ○ | — | — | | 243 |
| S12 | 0.500 | 0.050 | 0.200 | 0.250 | ○ | ○ | — | — | PEROVSKITE | 382 |
| S13 | 0.500 | 0.050 | 0.150 | 0.300 | ○ | ○ | — | — | | 767 |
| S14 | 0.500 | 0.050 | 0.100 | 0.350 | ○ | ○ | — | ○ | | 403 |
| S15* | 0.500 | 0.050 | 0.050 | 0.400 | ○ | ○ | — | ○ | $La_4M_3O_{10}$ OR $La_3M_2O_7$ | 103 |
| S16* | 0.500 | 0.150 | 0.200 | 0.150 | ○ | — | — | — | | 274 |
| S17 | 0.500 | 0.150 | 0.150 | 0.200 | ○ | ○ | — | — | PEROVSKITE | 397 |
| S18 | 0.500 | 0.150 | 0.100 | 0.250 | ○ | ○ | — | — | | 751 |
| S19 | 0.500 | 0.150 | 0.050 | 0.300 | ○ | ○ | — | — | | 868 |
| S20* | 0.500 | 0.150 | 0.000 | 0.350 | ○ | ○ | — | ○ | $La_4M_3O_{10}$ OR $La_3M_2O_7$ | 83 |
| S21 | 0.500 | 0.200 | 0.050 | 0.250 | ○ | ○ | — | — | | 1107 |
| S22 | 0.487 | 0.000 | 0.192 | 0.308 | ○ | ○ | — | — | PEROVSKITE | 784 |
| S23 | 0.512 | 0.000 | 0.207 | 0.293 | ○ | ○ | — | — | | 306 |

FIG. 4

| SAMPLE | La$_a$Co$_b$Fe$_c$Ni$_d$O$_x$ ELEMENTS (MOLE RATIO) | | | | B CONST. ($K^{-1}$) | THERMAL ELECTROMOTIVE FORCE 770°C ($\mu V/K$) |
|---|---|---|---|---|---|---|
| | $a$ | $b$ | $c$ | $d$ | | |
| S6 | 0.500 | 0.000 | 0.200 | 0.300 | −12 | −5.4 |
| S12 | 0.500 | 0.050 | 0.200 | 0.250 | 156 | −8.6 |
| S18 | 0.500 | 0.150 | 0.100 | 0.250 | 48 | −9.7 |
| S21 | 0.500 | 0.200 | 0.050 | 0.250 | −44 | −11 |
| S24* | 0.500 | 0.250 | 0.000 | 0.250 | −105 | −14.1 |

| SAMPLE | La$_a$Co$_b$Fe$_c$Ni$_d$O$_x$ ELEMENTS (MOLE RATIO) | | | | CRYSTALLINE PHASE (wt%) | | | CONDUCTIVITY σ 25°C (S/cm) |
|---|---|---|---|---|---|---|---|---|
| | a | b | c | d | LaMO$_3$ | La$_4$M$_3$O$_{10}$ OR La$_3$M$_2$O$_7$ | NiO | |
| S2* | 0.500 | 0.000 | 0.320 | 0.180 | 100 | UNDETECTED | UNDETECTED | 56 |
| S6 | 0.500 | 0.000 | 0.200 | 0.300 | 99.4 | 0.6 | UNDETECTED | 581 |
| S7 | 0.500 | 0.000 | 0.150 | 0.350 | 63.3 | 35.2 | 1.5 | 821 |

FIG. 10

(Ni CONTENT RANGES WHERE PEROVSKITE PRIMARY PHASE AND $La_4M_3O_{10}$ OR $La_3M_2O_7$ SECONDARY PHASE COEXIST)

ELECTRICALLY CONDUCTIVE OXIDE SINTERED COMPACT, MEMBER FOR ELECTRICAL CONDUCTION, AND GAS SENSOR

CROSS REFERENCE TO RELATED APPLICATIONS

This application is a National Stage of International Application No. PCT/JP2016/001790 filed Mar. 28, 2016, claiming priority based on Japanese Patent Application No. 2015-097958 filed May 13, 2015, the contents of all of which are incorporated herein by reference in their entirety.

TECHNICAL FIELD

The present invention relates to a conductive oxide sintered body, to a member for use as a conductive part (hereinafter referred to as conductive member) employing the sintered body, and to a gas sensor.

BACKGROUND ART

Generally, ceramic electronic devices have a ceramic substrate and electrodes disposed on the substrate, and such electrodes are formed of a metallic material. Such ceramic electronic devices include, for example, multi-layer ceramic capacitors equipped with an Ni electrode, a Pd electrode, or a Pt electrode; low temperature co-fired ceramic (LTCC) parts equipped with an Ag electrode, a Cu electrode, or an Ag—Pd electrode; piezo-actuators having a Pd electrode; semiconductor packages employing a W electrode; and spark plugs having an Ir electrode or a Pt electrode.

Among the above metal elements, Ni, Cu, and W must be fired with a ceramic substrate in a controlled atmosphere. Thus, difficulty is encountered in attaining characteristics intrinsic to the target ceramic substrate, and production cost rises, which is problematic. In the case of Ag, which has a low melting point (962° C.), the material of the ceramic substrate is limited. In addition, when the substrate is fired at low temperature, characteristics of the ceramic substrate may be impaired. Noble metals such as Pd, Ir, and Pt are expensive materials, making application of such material to wide electrodes difficult.

Patent Document 1 discloses, as an oxide electrode material, a lanthanum cobalt oxide having such a negative temperature characteristic that the resistance thereof is high at ambient temperature and lowers with rising temperature. Patent Document 2 discloses a lanthanum cobalt oxide having such a negative temperature characteristic that the resistance thereof is high at room temperature and the absolute value of B constant is large at high temperature. However, the conductive oxides disclosed in Patent Documents 1 and 2 exhibit high resistivity at room temperature; i.e., poor conductivity.

In the case where an electrode of a ceramic electronic device is formed from metal, the aforementioned problems occur. Thus, the present inventors previously tried to employ an oxide (ceramic) electrode instead of a metal electrode. However, conventional oxides have a conductivity which is considerably lower than that of metallic material, and a large absolute value of B constant (temperature coefficient). Therefore, difficulty is encountered in replacing a metal electrode with a ceramic electrode. Meanwhile, ruthenium oxides (e.g., $RuO_2$ and $SrRuO_3$) are known to have high conductivity, but are problematically expensive. Under such circumstances, the present applicant discloses in Patent Document 3 an oxide sintered body which has high conductivity and a small absolute value of B constant (temperature coefficient) and which is suited for a conductive material. Also, Patent Documents 4 to 6 disclose various perovskite-type conductive oxides.

PRIOR ART DOCUMENTS

Patent Documents

Patent Document 1: Japanese Patent No. 3286906
Patent Document 2: Japanese Patent Application Laid-Open (kokai) No. 2002-087882
Patent Document 3: WO 2013/150779
Patent Document 4: Japanese Patent Application Laid-Open (kokai) No. 1990-269949
Patent Document 5: Japanese Patent Application Laid-Open (kokai) No. 1991-165253
Patent Document 6: Japanese Patent Application Laid-Open (kokai) No. 2002-084006

SUMMARY OF THE INVENTION

Problem to be Solved by the Invention

However, in many cases, conventional conductive oxides may fail to exhibit high conductivity. Thus, there is demand for a conductive oxide sintered body having higher conductivity.

Means for Solving the Problem

The present invention has been conceived to solve the aforementioned problems and can be embodied in the following modes.

(1) In one mode of the present invention, there is provided a conductive oxide sintered body. A characteristic feature of the conductive oxide sintered body resides in that the sintered body contains a primary phase formed of a perovskite-type conductive oxide containing at least La, Fe, and Ni; and a secondary phase formed of an $La_4M_3O_{10}$ phase or an $La_3M_2O_7$ phase (M=Co, Fe, Ni). According to the conductive oxide sintered body, there can be provided a conductive oxide sintered body having high conductivity.

(2) In the above conductive oxide sintered body, the conductive oxide sintered body may be represented by formula:

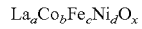

$La_aCo_bFe_cNi_dO_x$ (a+b+c+d=1, 1.25≤x≤1.75), and a, b, c, and d may satisfy the conditions:

0.487≤a≤0.512,

0≤b≤0.200, 0.050≤c≤0.230, and 0.200≤d≤0.350.

According to the feature, there can be provided a conductive oxide sintered body having a conductivity of 300 S/cm or higher at room temperature.

(3) The above conductive oxide sintered body may contain substantially no alkaline earth metal element. According to this feature, diffusion of an alkaline earth metal element from an electrode formed of the conductive oxide sintered body to another member (e.g., a member in a gas sensor) can be prevented. Thus, impairment in electrode performance, which would otherwise occur due to diffusion of an alkaline earth metal element, can be prevented. Also, impairment in performance (e.g., impedance of a gas sensor) of a device including an electrode formed of a conductive oxide sintered body and other members can be prevented.

The present invention can be realized as various embodiments. Such embodiments include, for example, a conductive oxide sintered body, various devices and materials each employing the conductive oxide sintered body, such as electrodes, electric wirings, conductive members, gas sensors (specifically, an oxygen sensor and an NOx sensor), thermoelectric material, heater material, and temperature-sensing elements, and production methods therefor.

BRIEF DESCRIPTION OF THE DRAWINGS

FIG. 4 is a table showing compositions and characteristics of various samples.

FIG. 10 is a table showing crystalline phase ratios of typical samples.

MODES FOR CARRYING OUT THE INVENTION

Figure 1:
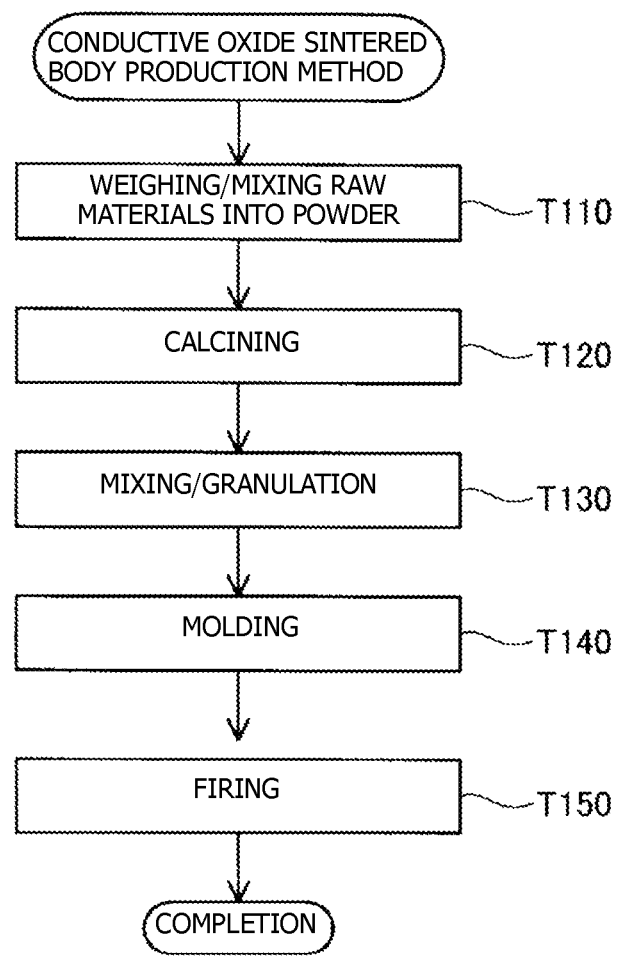
FIG. 1 is a flowchart showing a method of producing a conductive oxide sintered body of an embodiment.

A. Conductive Oxide Sintered Body and Compositional Proportions Thereof

The conductive oxide sintered body according to an embodiment of the present invention is a sintered body which contains a primary phase formed of a perovskite-type conductive oxide containing at least La, Fe, and Ni; and a secondary phase formed of an $La_4M_3O_{10}$ phase or an $La_3M_2O_7$ phase (M=Co, Fe, Ni). As used herein, the term "primary phase" refers to a crystalline phase which exhibits a maximum peak intensity in XRD. Among various perovskite-type oxides, conductive oxides containing La, Fe, and Ni exhibit high conductivity and a small absolute value of B constant (temperature coefficient), which are suitable characteristics. Therefore, such conductive oxides are suited for electrode materials. The present inventors have found that a conductive oxide sintered body which contains a primary phase formed of such a perovskite-type conductive oxide, and a secondary phase formed of an $La_4M_3O_{10}$ phase or an $La_3M_2O_7$ phase (M=Co, Fe, Ni) exhibits particularly high conductivity. Notably, in the case where the crystalline phase of a perovskite-type conductive oxide (referred to simply as "perovskite phase") is not a primary phase, the total conductivity of the sintered body decreases. Thus, the primary phase is preferably a perovskite phase.

The conductive oxide sintered body according to an embodiment of the present invention preferably satisfies the following compositional formula:

$$La_aCo_bFe_cNi_dO_x \qquad (1)$$

(a+b+c+d=1, 1.25≤x≤1.75). The coefficients a, b, c, and d preferably satisfy the following conditions:

$$0.487 \le a \le 0.512 \qquad (2a),$$

$$0 \le b \le 0.200 \qquad (2b),$$

$$0.050 \le c \le 0.230 \qquad (2c),$$

and $$0.200 \le d \le 0.350 \qquad (2d).$$

When the above relationships (2a) to (2d) are satisfied, a conductivity of 300 S/cm or higher at room temperature can be attained. As used herein, the concept "conductivity at room temperature (also referred to as room temperature conductivity)" refers to a conductivity measured at 25° C. When the coefficients a, b, c, and d fall outside the above ranges, a room temperature conductivity of 300 S/cm or higher fails to be attained, or neither $La_4M_3O_{10}$ phase nor $La_3M_2O_7$ phase may fail to be formed, which is not preferred.

In addition, the coefficients a, b, c, and d more preferably satisfy the conditions:

$$0.487 \le a \le 0.510 \qquad (3a),$$

$$0 \le b \le 0.200 \qquad (3b),$$

$$0.050 \le c \le 0.230 \qquad (3c),$$

and $$0.250 \le d \le 0.300 \qquad (3d).$$

When the coefficients a, b, c, and d satisfy the above conditions, the room temperature conductivity can be further enhanced.

In the case where the oxide sintered body having the above composition is completely formed of a perovskite phase, the coefficient "x" with respect to O (oxygen) is theoretically 1.50. However, the oxide sintered body includes not only a primary phase formed of a perovskite phase but also a secondary phase formed of a non-perovskite phase. Thus, the range of x is defined as a typical range: 1.25≤x≤1.75.

Notably, the conductive oxide sintered body according to the embodiment of the present invention may further contain a very small amount of alkaline earth metal element, so long as the conductivity thereof is not impaired. However, preferably, the conductive oxide sintered body contains substantially no alkaline earth metal element. As used herein, the concept "substantially containing no alkaline earth metal element" refers to an alkaline earth metal element content of 0.3% or lower, which is determined through element analysis via ICP emission spectrometry. The ICP emission spectrometry is carried out according to JIS K0116. Analytical samples are preliminarily treated through the hydrochloric acid dissolution technique. In the case where a conductive oxide sintered body containing an alkaline earth metal element such as Sr is employed as an electrode of a gas sensor (e.g., an oxygen sensor), the alkaline earth metal element diffuses into the gas sensor substrate (e.g., yttria-stabilized zirconia) during long-term use under high temperature actual working conditions. In such a case, impairment in performance of the electrode due to diffusion of the alkaline earth metal element, or performance of the gas sensor (e.g., reduction in impedance) may occur. Thus, preferably, the conductive oxide sintered body contains substantially no alkaline earth metal element.

The oxide sintered body according to the embodiment of the present invention may be employed as a metallic material substitute in electrodes, electric wirings, conductive members, gas sensors, thermoelectric material, heater material, and temperature-sensing elements. In one specific example, the aforementioned conductive member may be produced by forming, on the surface of a ceramic substrate, a conductor layer made of the conductive oxide sintered body. The aforementioned gas sensors may be fabricated to be equipped with an electrode formed of the conductive oxide sintered body.

B. Manufacturing Method

FIG. 1 is a flowchart showing a method of producing a conductive oxide sintered body of an embodiment of the present invention. In step T110, raw materials in powder form of the conductive oxide sintered body are weighed, mixed under wet conditions, and dried, to thereby prepare a raw material mixture powder. Examples of powder form raw materials which may be employed in the step include $La(OH)_3$, $Co_3O_4$, $Fe_2O_3$, and $NiO$. These material powders preferably have a purity of 99% or higher. As an La source, $La_2O_3$ may be used instead of $La(OH)_3$. However, use of $La(OH)_3$ or no use of $La_2O_3$ is preferred. The reason for this is that difficulty is encountered in precise mixing of $La_2O_3$ due to water absorbability thereof, possibly causing a drop in conductivity and reproducibility. In step T120, the raw material mixture powder is calcined in air at 700 to 1,200° C. for 1 to 5 hours, to thereby form a calcined powder. In step T130, an appropriate amount of organic binder is added to the calcined powder, and the mixture is put into a resin pot with a dispersion medium (e.g., ethanol). The resultant mixture is mixed and pulverized by means of zirconia balls under wet conditions, to thereby yield a slurry. In step T130, the thus-obtained slurry is dried at 80° C. for about 2 hours, and the dried product is granulated through a 250-μm mesh, to thereby yield a granule powder. In step T140, the thus-obtained granule powder is molded by means of a press machine. In step T150, the obtained compact is fired in air for 1 to 5 hours at a firing temperature (1,300 to 1,600° C.) higher than the calcination temperature employed in step T120, to thereby yield a sintered conductive oxide body. If required, the surface of the conductive oxide sintered body may be polished after firing.

Figure 2:
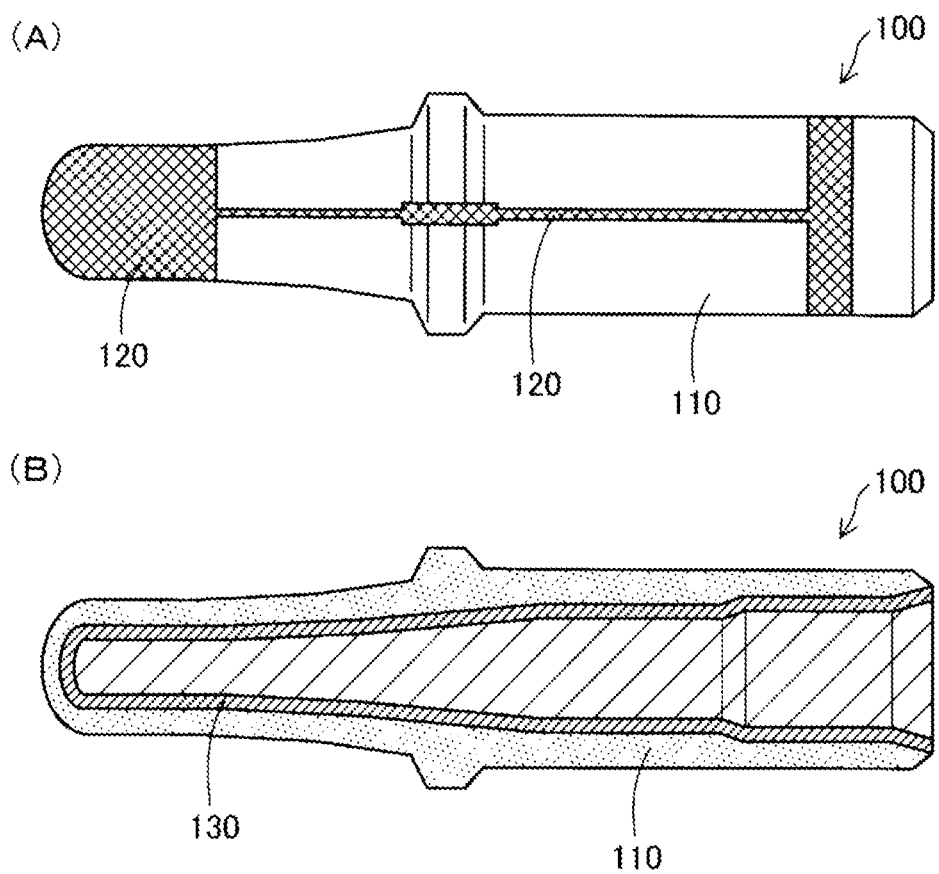
FIG. 2(A) is a front view of a gas sensor employing the conductive oxide sintered body.
FIG. 2(B) is a cross-section thereof.

FIG. 2(A) is a front view of a gas sensor employing the conductive oxide sintered body, and FIG. 2(B) is a cross-section thereof. A gas sensor 100 is an oxygen sensor, extending along a longitudinal direction, and includes a ceramic substrate 110 having a shape of a bottomed tube, the ceramic being yttria-stabilized zirconia; a noble metal outside electrode 120 formed on the outer surface of the substrate 110; and a standard electrode 130 (reference electrode) formed on the inner surface of the 110. The standard electrode 130 is a conductor layer formed of a conductive oxide sintered body. In the gas sensor, the standard electrode 130 is provided on virtually the entire inner surface of the substrate 110. The outside electrode 120 comes into contact with a measurement gas (e.g., exhaust gas), while the standard electrode 130 serves as a reference electrode which comes into contact with a reference gas (e.g., air) having a reference oxygen concentration for determination of oxygen concentration.

Figure 3:
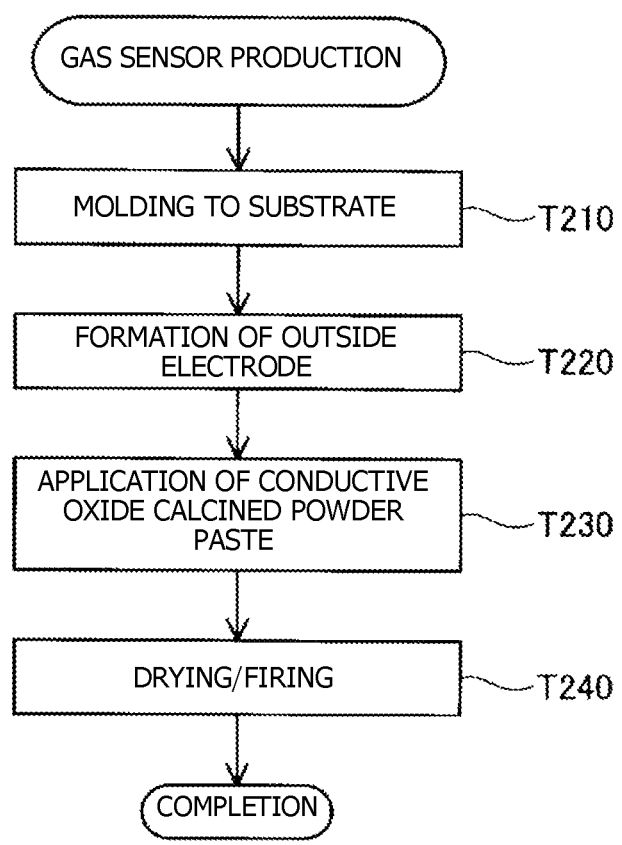
FIG. 3 is a flowchart showing a method of producing a gas sensor.

FIG. 3 is a flowchart showing a method of producing the gas sensor 100. In step T210, a material of the substrate 110 (e.g., yttria-stabilized zirconia powder) is press-molded, and the molded product is cut into a shape (tube) shown in FIG. 2, to thereby yield a green product (an unsintered molded product). In step T220, the outside electrode 120 is provided on the surface of the green product by use of a Pt paste or an Au paste through printing or dipping. In step T230, the calcined powder of the conductive oxide formed in steps T110 and T120 shown in FIG. 1 is dissolved in a solvent such as terpineol or butyl carbitol with a binder such as ethylcellulose, to thereby prepare a paste. The paste is applied onto the inner surface of the sintered yttria-stabilized zirconia tube. In step T240, the zirconia tube is dried and fired in air at 1,250 to 1,600° C. for 1 to 5 hours, to thereby produce a gas sensor. Notably, conditions employed in the production methods of FIGS. 1 and 3 are merely examples, and those skilled in the art can appropriately modify them in accordance with use and the like of the products.

C. Examples and Comparative Examples

FIG. 4 shows compositions and characteristics of various samples of the Examples and Comparative Examples. In FIG. 4, sample numbers with a symbol "*" denote samples of the Comparative Examples, and sample numbers with no symbol "*" denote samples of the Examples. The oxide sintered body corresponding to each sample was produced according to the production method shown in FIG. 1. The sintered body was surface-polished, to thereby yield a rectangular parallelpiped sample (3.0 mm×3.0 mm×15.0 mm). In step T110, raw materials were weighed and mixed at a composition shown in FIG. 4.

FIG. 4 shows the composition of each sample, the results of identification of crystalline phases contained in the sintered body, and room temperature conductivity of each sample. The "$LaMO_3$" in the column of "CRYSTALLINE PHASE" refers to a perovskite-type oxide. The "$La_2MO_4$" in the column refers to a complex oxide having an $A_2BO_4$-type structure. The complex oxide having an $A_2BO_4$-type structure is also called a "layered perovskite-type complex oxide." As used herein, the term "perovskite-type oxide" without a prefix "layered" refers to an oxide having an $ABO_3$-type structure. In the table, "O" refers to "detection of a relevant crystalline phase," and "-" refers to "detection of no crystalline phase." Identification of a crystalline phase and determination of room temperature conductivity were carried out in the following manner.

<XRD Measurement>

A sintered body of each sample was pulverized, and the obtained powder was subjected to powder X-ray diffractometry (XRD), so as to identify a crystalline phase. Measurement conditions are as follows.

Apparatus: RINT-TTR-III (Rigaku Corporation, gonio radius: 285 mm)

Optical system: centralized optical system, Bragg-Brentano type

X-ray output: 50 kV-300 mA

Other conditions: divergence slit: ⅓°, vertical divergence limitation slit: 10 mm, scattering slit: ⅓°, light receiving slit: 0.3 mm, scanning mode: FI, counting time: 2.0 sec, step width: 0.0200°, scan axis: 2θ/θ, scan range: 20.00° to 120.00°, rotation: yes.

Figure 5:
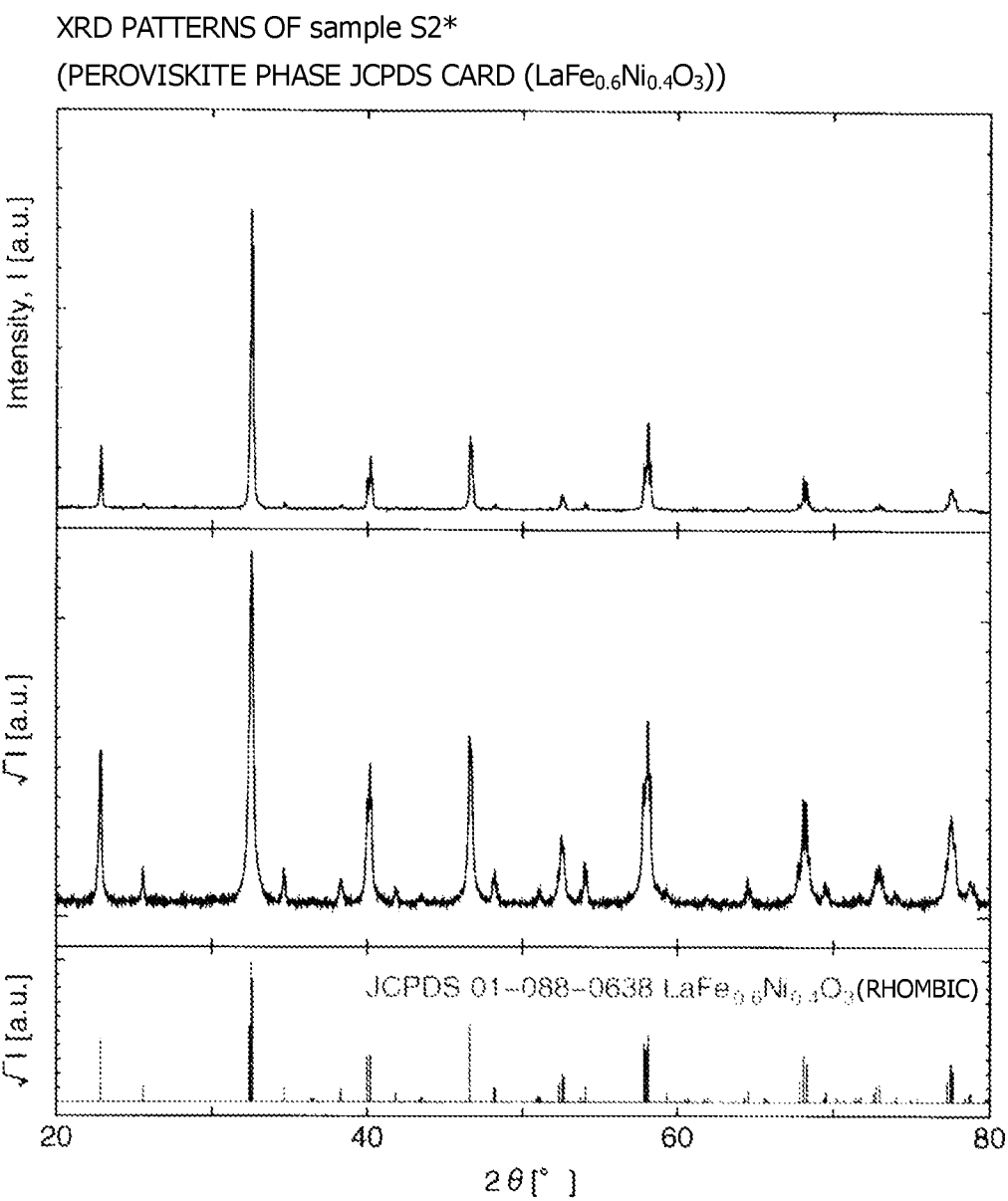
FIG. 5 is a chart showing XRD patterns of sample S2.

FIG. 5 is a chart showing XRD patterns of sample S2. In FIG. 5, the upper chart shows XRD intensity I of sample S2, the middle chart the square root of the XRD intensity I, and the bottom chart an XRD pattern of a perovskite phase (specifically $LaFe_{0.6}Ni_{0.4}O_3$) (JCPDS card). No crystalline phase other than the perovskite phase was detected in sample S2.

Figure 6:
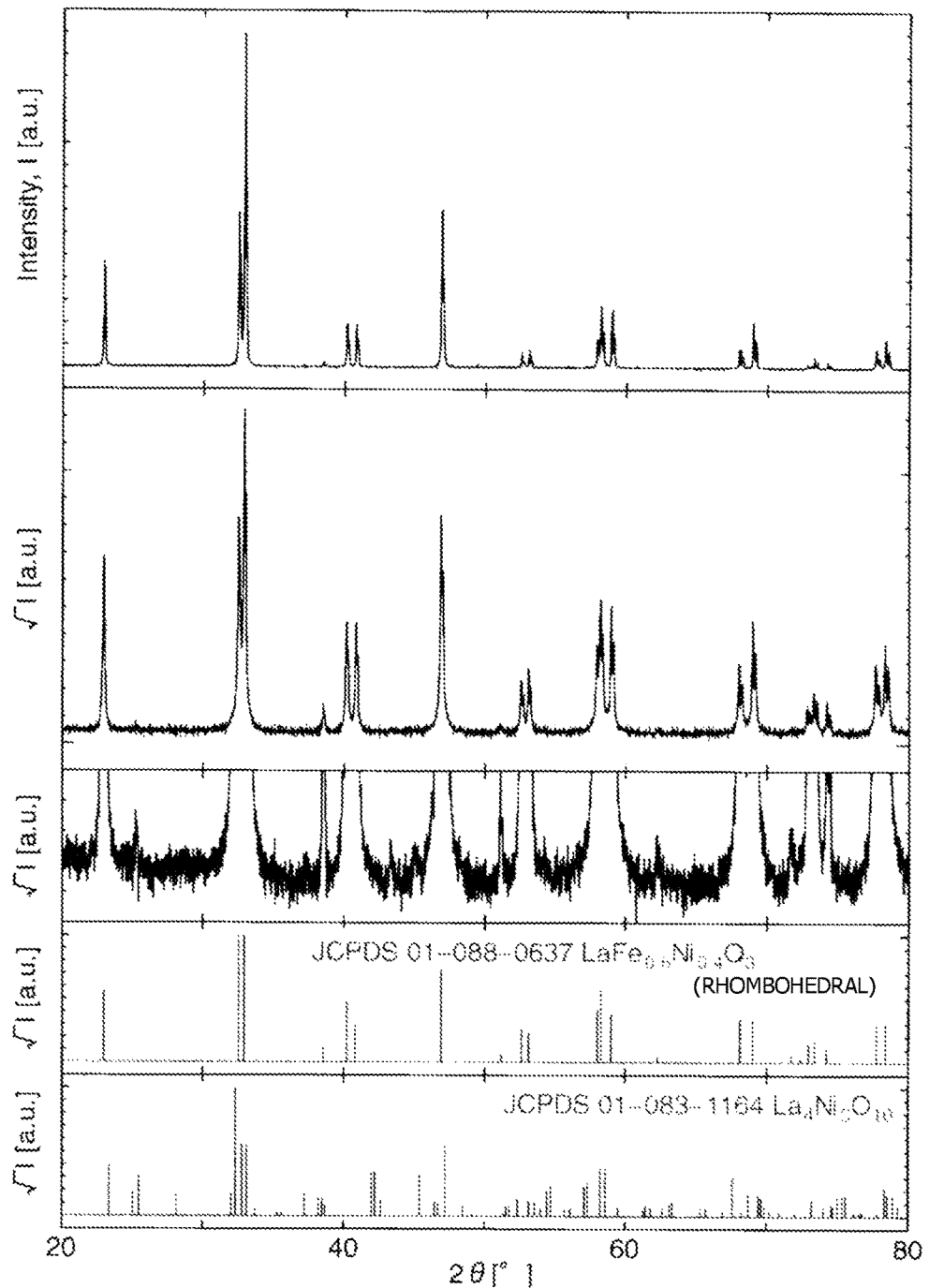
FIG. 6 is a chart showing XRD patterns of sample S6.

FIG. 6 is a chart showing XRD patterns of sample S6. In FIG. 6, the uppermost chart shows XRD intensity I of sample S6, the second chart the square root of the XRD intensity I, the third chart an enlarged image of the second chart, the fourth chart the XRD pattern of a perovskite phase (specifically $LaFe_{0.6}Ni_{0.1}O_3$), and the bottom chart an XRD pattern of an $La_4M_3O_{10}$ phase (specifically $La_4Ni_3O_{10}$). In addition to the perovskite phase, an $La_4Ni_3O_{10}$ phase was detected in sample S6. The crystalline phase exhibiting the maximum peak was found to be a perovskite phase.

Figure 7:
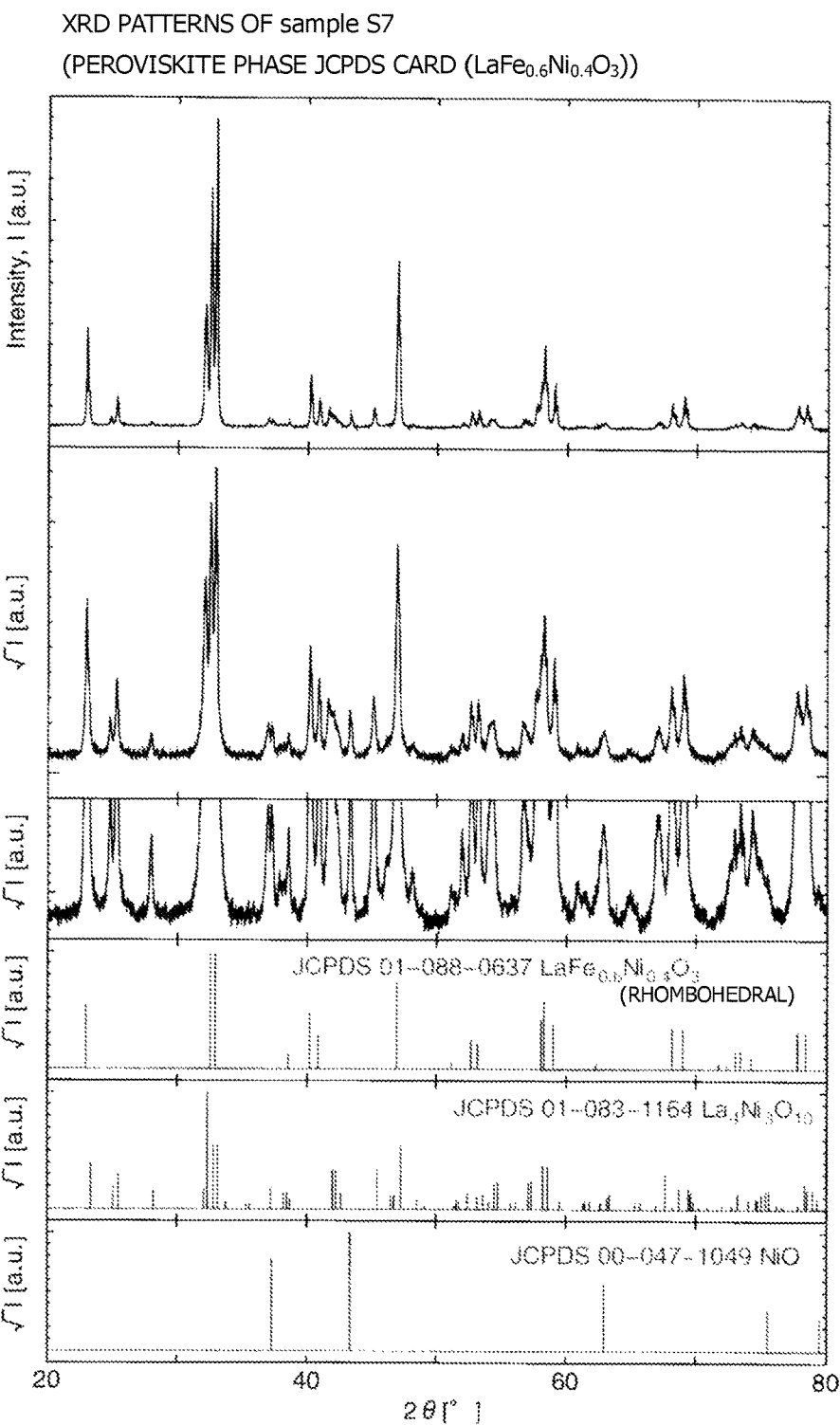
FIG. 7 is a chart showing XRD patterns of sample S7.

FIG. 7 is a chart showing XRD patterns of sample S7. In FIG. 7, the uppermost chart shows XRD intensity I of sample S7, the second chart the square root of the XRD intensity I, the third chart an enlarged image of the second chart, the fourth chart the XRD pattern of a perovskite phase (specifically $LaFe_{0.6}Ni_{0.4}O_3$), the fifth chart the XRD pattern of an $La_4M_3O_{10}$ phase (specifically $La_4Ni_3O_{10}$), and the bottom chart an XRD pattern of an NiO phase. In addition to the perovskite phase, an $La_4Ni_3O_{10}$ phase and an NiO phase were detected in sample S7. The crystalline phase exhibiting the maximum peak was found to be a perovskite phase. The above results of identification of crystalline phases in each sample are shown in the column of "CRYSTALLINE PHASE IDENTIFICATION" in FIG. 4.

<Conductivity Measurement>

Conductivity was measured through the DC four-terminal method. The electrodes and electrode wire made of Pt were employed in the conductivity measurement. The conductivity was measured by means of a voltage/current generator (Monitor 6242, product of ADC Corporation).

All the samples S4 to S7, S12 to S14, S17 to S19, and S21 to S23 corresponding to Examples shown in FIG. 4 satisfy compositional relationships given by formulas (1) and (2a) to (2d). These samples, exhibiting a high room temperature conductivity of 300 S/cm or higher, are preferred. In contrast, samples S1 to S3, S8 to S11, S15 to S16, and S20 corresponding to Comparative Examples exhibited a room temperature conductivity lower than the conductivities of the samples corresponding Examples.

Samples S4 to S6, S12 to S13, S17 to S19, S21, and S22 (i.e., samples S4 to S7, S12 to S14, S17 to S19, and S21 to S23 corresponding Examples, excluding samples S7, S14, and S23), all satisfy compositional relationships given by formulas (1) and (3a) to (3d). These samples, exhibiting a higher room temperature conductivity of 350 S/cm or higher, are particularly preferred.

Figures 8, 9:
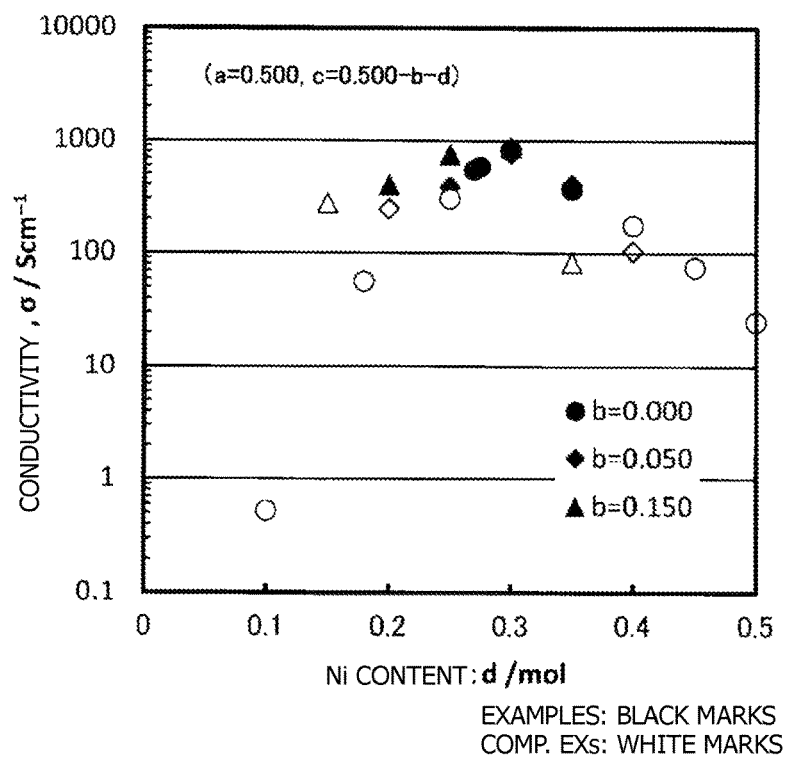
FIG. 8 is a graph showing a relationship between Ni content and conductivity at room temperature.
FIG. 9 is a table showing B constants of typical samples.

FIG. 8 is a graph showing the relationship between Ni content and room temperature conductivity. The graph shows the analytical results of samples satisfying the conditions: coefficient a=0.500 and coefficient c=(0.500−b−d), among the samples listed in FIG. 4. In the graph, the black marks denote samples corresponding to Examples, and the white marks denote samples corresponding to Comparative Examples. As is clear from the graph, coefficient d of Ni preferably satisfies the range: 0.200≤d≤0.350, more preferably the range: 0.250≤d≤0.300.

FIG. 9 is a table showing B constants and thermal electromotive force values of typical samples S6, S12, S18, and S21 selected from the samples listed in FIG. 4, and additional sample S24 (Comparative Example). All of these samples satisfy the condition: a=0.500, but have different coefficient b values. B constant and thermal electromotive force were determined in the following manner.

<Measurement of B Constant>

Conductivity of a sample was measured at 25° C. and 870° C. through the aforementioned <Conductivity measurement>. B constant ($K^{-1}$) was calculated by the following formula:

$$B\ \text{constant} = \ln(\rho1/\rho2)/(1/T1-1/T2) \quad (4)$$

$$\rho1 = 1/\sigma1$$

$$\rho2 = 1/\sigma2$$

ρ1: resistivity (Ωcm) at absolute temperature T1 (K)
ρ2: resistivity (Ωcm) at absolute temperature T2 (K)
σ1: conductivity (S/cm) at absolute temperature T1 (K)
σ2: conductivity (S/cm) at absolute temperature T2 (K)
T1=298.15 (K)
T2=1,143.15 (K)

<Measurement of Thermal Electromotive Force>

Thermal electromotive force was measured through the steady-state direct current method. To each sample (3.0 mm×3.0 mm×15.0 mm), two Pt wires were attached such that the sample was wound by each Pt wire at a position slightly apart from a longitudinal end toward the center with a specific interwire distance. The two Pt wires served as electrodes for measuring the voltage to determine conductivity. Also, Au was deposited on two ends of the sample through sputtering, and an outside Pt electrode (Pt plate or Pt net) was attached to each Au-deposited end. In this state, each end of the sample was fixed by a quartz tube in a sandwich manner. During measurement, a steady-state current was caused to flow between the two outside Pt electrodes, and high-temperature air was fed to one quartz tube, to thereby generate temperature difference between the electrodes. Then, an R thermocouple (Pt—Pt13Rh) was attached to the outside Pt electrodes, to thereby measure the temperature difference. By varying the air flow, the temperature difference was generated step-by-step. The voltage-temperature difference correlation was determined, and thermal electromotive force at 770° C. was derived through the least-squares method. The above measurement was performed by means of RZ2001k (product of Ozawa Science) under atmospheric conditions.

Typical samples are shown in FIG. 9. As shown in the table, these samples have a sufficiently small B constant absolute value of 200 $K^{-1}$ or less, indicating that the samples exhibit satisfactorily high conductivity even under temperature variation. Although other samples of Examples are not listed in the table, the above tendency was confirmed. In other words, samples S4 to S7, S12 to S14, S17 to S19, and S21 to S23 have a B constant suited for use as a conductive layer.

The typical samples shown in FIG. 9 exhibited an absolute value of the thermal electromotive force at 770° C. of 15 μV/K or less. In particular, samples S6, S18, and S21 of Examples exhibited an excellent value of 11 μV/K or less.

Thus, a conductive oxide sintered body exhibiting a sufficiently small absolute value of thermal electromotive force at 770° C. is particularly suited for use as an electrode of an oxygen sensor. More specifically, in an oxygen sensor, the difference in temperature between two ends of an electrode may rise to about 500° C. By use of a conductive oxide sintered body exhibiting a small absolute value of thermal electromotive force at 770° C. as an electrode material, noise generation in response to the difference in temperature between two ends of an electrode can be sufficiently reduced, to thereby suppress an increase in measurement error. Although other samples of Examples are not listed in the table, all these samples were found to exhibit a thermal electromotive force absolute value of 11 μV/K or less.

FIG. 10 is a table showing crystalline phase proportions of typical samples S2, S6, and S7. The crystalline phase proportions were calculated through multiple-phase Rietvelt analysis.

<Rietvelt Analysis>

Rietvelt analysis was performed by means of Rietan-FP code. An XRD pattern obtained through the aforementioned XRD was subjected to multiple-phase Rietvelt analysis with Rietan-FP code, to thereby calculate the ratio of primary phase to secondary phase. Split Pearson VII function was selected as a peak function employed in refinement. Space group Pnma (#62) was employed with respect to orthorhombic $LaMO_3$ phase, space group R-3c (#167) rhombohedral $LaMO_3$ phase, space group Fmmm (#69) $La_4M_3O_{10}$ phase, and space group Fm-3c (#225) NiO phase. Regarding "split Pearson VII function," see H. Toraya, J. Appl. Crystallogr. 23, 485 (1990).

All samples S2, S6, and S7 shown in FIG. 10 have a=0.500 and b=0.0, but have different coefficient c of Fe and coefficient d of Ni. As coefficient c decreases and coefficient d increases, the proportion of perovskite phase ($LaMO_3$ phase) decreases, and $La_4M_3O_{10}$ phase or $La_3M_2O_7$ phase (M=Co, Fe, Ni) gradually generates. When coefficient d increases to about 0.35, NiO phase generates in addition to $La_4M_3O_{10}$ phase or $La_3M_2O_7$ phase. Generation of $La_4M_3O_{10}$ phase or $La_3M_2O_7$ phase is preferred, since conductivity at room temperature drastically rises. The $La_4M_3O_{10}$ phase content or the $La_3M_2O_7$ phase content is preferably 36 wt. % or lower (see sample S7), since, when the $La_4M_3O_{10}$ phase content or the $La_3M_2O_7$ phase content is in excess of 36 wt. %, the conductive perovskite phase content decreases excessively, and the conductivity of the sintered body conceivably decreases. For example, sample S8 in FIG. 4 has coefficient d greater than that of sample S7, and the $La_4M_3O_{10}$ phase content or the $La_3M_2O_7$ phase content is higher than 36 wt. %. The room temperature conductivity of sample S8 is lower than that of sample S6, conceivably because the $La_4M_3O_{10}$ phase content or the $La_3M_2O_7$ phase content is higher than 36 wt. %.

Conceivably, the tendency described in relation to FIG. 10 is observed not only in the case of a=0.500 and b=0.0, but also for other values of compositional coefficients a and b. In other words, in the oxide sintered body represented by the compositional formula (1), the crystalline phases present therein change in accordance with the changes in ratio of coefficient c to d, when coefficients a and b are constant. In an area where coefficient d is small (i.e., amount of Ni is small), the area of the sintered body is formed of a perovskite single phase and contains no secondary phase. In contrast, as coefficient d increases (i.e., coefficient c decreases), $La_4M_3O_{10}$ phase or $La_3M_2O_7$ phase (M=Co, Fe, Ni) generates in addition to perovskite phase. When coefficient d further increases (i.e., coefficient c decreases), NiO phase generates in addition to $La_4M_3O_{10}$ phase or $La_3M_2O_7$ phase (M=Co, Fe, Ni), and perovskite phase decreases further. When coefficient d increases yet further (i.e., coefficient c decreases), perovskite phase disappears, and $La_2NiO_4$ phase generates (see samples S9 and S10 in FIG. 4).

Among various crystalline phase proportions, the conductivity of the sintered body is the highest when the sintered body includes a perovskite primary phase as well as $La_4M_3O_{10}$ phase or $La_3M_2O_7$ phase. In contrast, when the primary phase is not formed of a perovskite phase, conductivity decreases. The conductivity depends not only on the ratio of coefficient c to coefficient d (i.e., crystalline phase proportions) but also on coefficient b. However, when coefficient b is constant, conductivity and crystalline phase vary depending on the ratio of coefficient c to coefficient d at any value of coefficient b. However, as coefficient b decreases, the value of coefficient d at which $La_4M_3O_{10}$ phase or $La_3M_2O_7$ phase starts to generate increases (i.e., coefficient c decreases).

Figure 11:
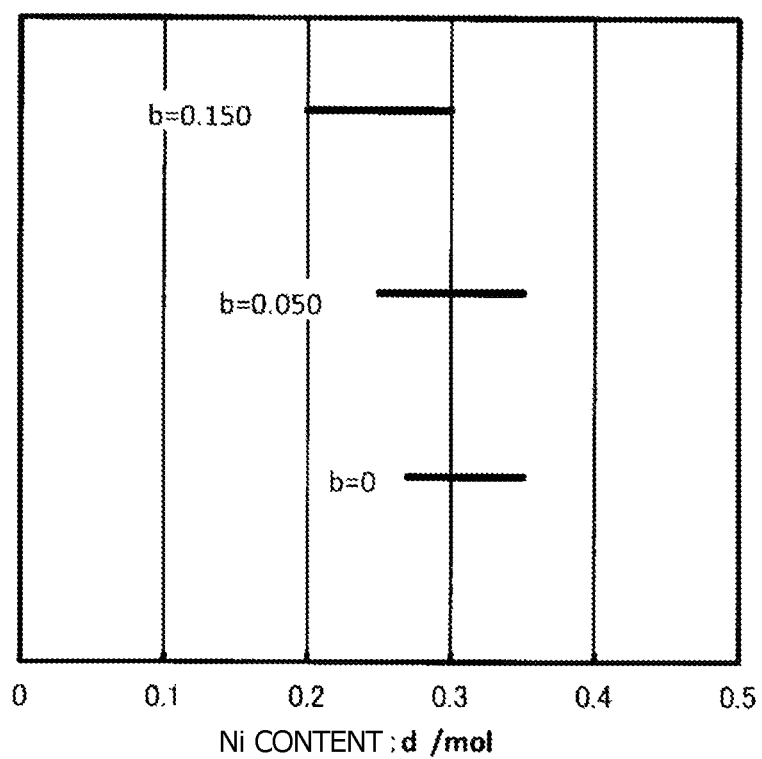
FIG. 11 is a graph showing Ni content ranges where a primary phase formed of a perovskite phase and a secondary phase formed of an $La_4M_3O_{10}$ phase or an $La_3M_2O_7$ phase coexist.

FIG. 11 is a graph showing Ni content ranges where a primary phase formed of a perovskite phase and a secondary phase formed of an $La_4M_3O_{10}$ phase or an $La_3M_2O_7$ phase coexist. When coefficient b of Co is 0, both primary and secondary phases coexist within a range: $0.270 \leq d \leq 0.350$. When coefficient b is 0.050, both primary and secondary phases coexist within a range: $0.250 \leq d \leq 0.350$. When coefficient b is 0.150, both primary and secondary phases coexist within a range: $0.200 \leq d \leq 0.300$. Thus, in the composition represented by formula (1), a primary phase formed of a perovskite phase and a secondary phase formed of $La_4M_3O_{10}$ phase or $La_3M_2O_7$ phase can be co-present by appropriately tuning coefficient d of Ni with respect to coefficient b of Co.

FIG. 12(A) is a Co—Ni—Fe ternary system phase diagram of samples shown in FIG. 4. In FIG. 12(A) shows proportions of coefficient b, c, and d of the other three elements (Co, Ni, Fe) regarding each of samples S1 to S21 (constant coefficient a of La), among samples S1 to S23 shown in FIG. 4. For the purpose of illustration, coefficients B, C, and D are used instead of coefficients b, c, and d of formula (1). Coefficients B, C, and D are doubled values of coefficients b, c, and d. Specifically, a is 0.500, and B, C, and D are 2b, 2c, and 2d, respectively. The sum of B+C+D is 1.0. In the diagram, black spots denote samples of Examples, and black triangles denote samples of Comparative Examples.

FIG. 12(B) is the same Co—Ni—Fe ternary system phase diagram in which the composition-related area R2 defined by the aforementioned formulas (2c) and (2d) is hatched. The composition-related area R2 is defined by the following formulas:

$$0 \leq B \leq 0.400 (0 \leq b \leq 0.200) \quad (5b);$$

$$0.100 \leq C \leq 0.460 (0.050 \leq c \leq 0.230) \quad (5c);$$

and $$0.400 \leq D \leq 0.700 (0.200 \leq d \leq 0.350) \quad (5d).$$

The formulas (5b) to (5d) are equivalent to the aforementioned formulas (2c) and (2d). The composition-related area R2 corresponds to an area including samples S4 to S7, S12 to S14, S17 to S19, and S21 of Examples shown in FIG. 4. In the composition-related area R2, both a primary phase formed of a perovskite phase and a secondary phase formed of $La_4M_3O_{10}$ phase or $La_3M_2O_7$ phase are generated, and high conductivity is attained.

FIG. 12(C) is the same Co—Ni—Fe ternary system phase diagram in which the composition-related area R3 defined by the aforementioned formulas (3a) to (3d) is hatched. The composition-related area R3 is defined by the following formulas:

$$0 \leq B \leq 0.400 (0 \leq b \leq 0.200) \quad (6b);$$

$$0.100 \leq C \leq 0.460 (0.050 \leq c \leq 0.230) \quad (6c);$$

and $$0.500 \leq D \leq 0.600 (0.250 \leq d \leq 0.300) \quad (6d).$$

The formulas (6b) to (6d) are equivalent to the aforementioned formulas (3c) and (3d). The composition-related area R3 corresponds to an area including samples S4 to S6, S12 and S13, S17 to S19, and S21 of Examples shown in FIG. 4. In the composition-related area R3, higher conductivity as compared with the composition-related area R2 shown in FIG. 12 (B) is attained.

When coefficient B (=2b) is greater than 0.400 (b>0.200), the absolute value of thermal electromotive force at 770° C. may rise excessively (see FIG. 9).

When coefficient C (=2c) is smaller than 0.100 (c<0.050), the absolute value of thermal electromotive force at 770° C. may rise excessively (see FIG. 9). When C is greater than 0.460 (c>0.230), $La_4M_3O_{10}$ phase or $La_3M_2O_7$ phase disappears, to thereby possibly reduce conductivity (see samples S3 and S4 in FIG. 4).

As described in relation to FIG. 10, when coefficient D (=2d) is greater than 0.700 (d>0.350), the $La_4M_3O_{10}$ phase content or the $La_3M_2O_7$ phase content exceeds 36 wt. %, to thereby possibly reduce conductivity. When coefficient D (=2d) is smaller than 0.400 (d<0.200), $La_4M_3O_{10}$ phase or $La_3M_2O_7$ phase disappears, to thereby possibly reduce conductivity (see samples S16 and S17 in FIG. 4).

Figure 12:
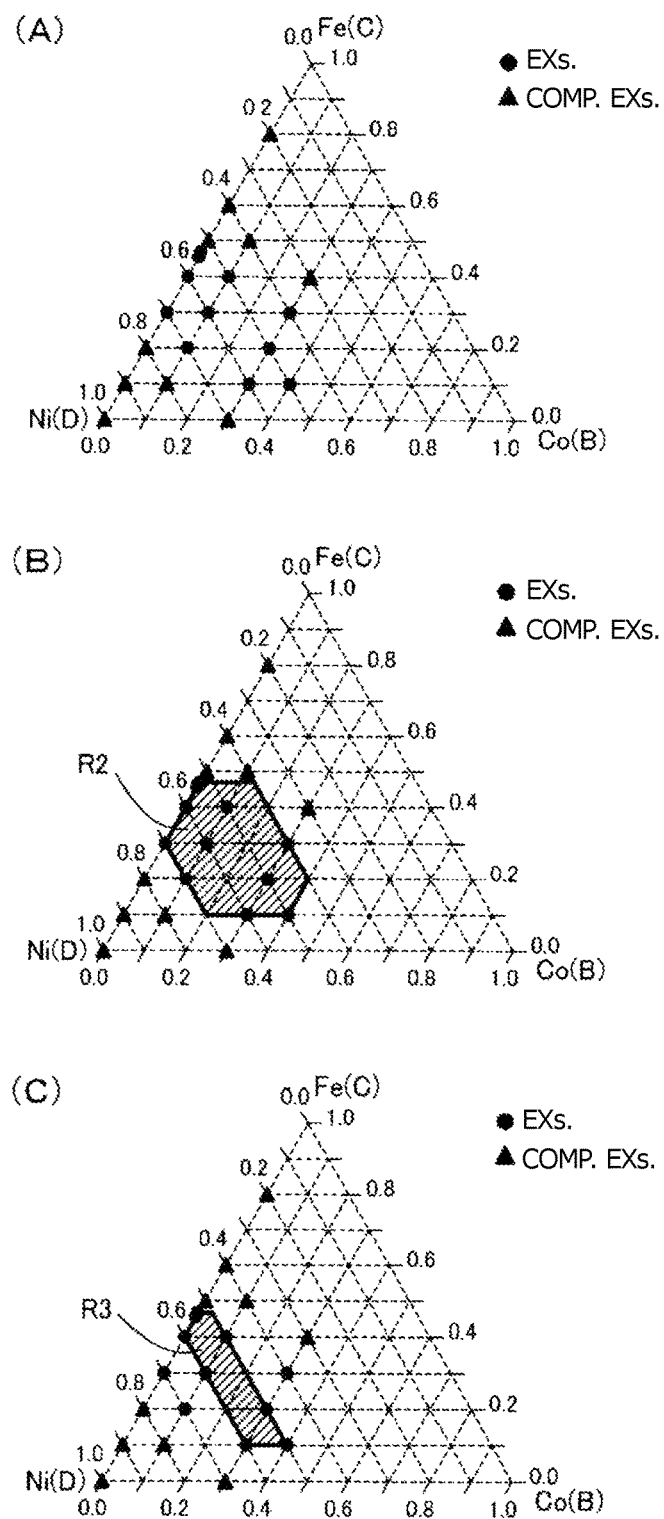
FIGS. 12(A), 12(B) and 12(C) are Co—Ni—Fe ternary system phase diagrams of samples S1 to S21.

The preferred composition-related areas R2 and R3, as described in relation to FIG. 12, are applied not only to the case where coefficient a is 0.500, but also conceivably to the case where coefficient a is a certain value other than 0.500. The reason for this is that the preferred range of coefficient a is limited to a narrow range of 0.487 to 0.512. Therefore, when coefficient a slightly varies within the above range, the preferred composition-related areas R2 and R3 are not conceivably impaired.

Variations

The aforementioned Examples and embodiments should not be construed as limiting the invention thereto. Needless to say, the present invention may be carried out in various modes, so long as those fall within the scope of the present invention.

DESCRIPTION OF REFERENCE NUMERALS

100: gas sensor
110: substrate
120: outside electrode
130: reference electrode (conductor layer)

The invention claimed is:

1. A gas sensor, characterized by having an electrode formed of a conductive oxide sintered body which contains a primary phase formed of a perovskite oxide containing at least La, Fe, and Ni; and a secondary phase formed of an $La_4M_3O_{10}$ phase or an $La_3M_2O_7$ phase (M=Co, Fe, Ni), wherein:

the conductive oxide sintered body has a conductivity of 300 S/cm or higher at room temperature, the conductive oxide sintered body does not contain an NiO phase, and the conductive oxide sintered body is represented by formula:

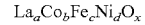

$(a+b+c+d=1, 1.25 \leq x \leq 1.75)$, and a, b, c, and d satisfy the conditions:

$$0.487 \leq a \leq 0.512,$$

$$0 \leq b \leq 0.200,$$

$$0.050 \leq c \leq 0.230, \text{ and}$$

$$0.200 \leq d \leq 308.$$

2. A gas sensor according to claim 1, wherein the conductive oxide sintered body contains substantially no alkaline earth metal element.

* * * * *